United States Patent [19]

Bewicke

[11] Patent Number: 6,080,410

[45] Date of Patent: ***Jun. 27, 2000

[54] METHOD FOR REDUCING DAILY STRESS AND ANXIETY IN ADULTS

[75] Inventor: Calvery M. Bewicke, San Anselmo, Calif.

[73] Assignee: Natrol, Inc., Chatsworth, Calif.

[ * ] Notice: This patent is subject to a terminal disclaimer.

[21] Appl. No.: 09/102,165

[22] Filed: Jun. 22, 1998

Related U.S. Application Data

[63] Continuation-in-part of application No. 08/818,931, Mar. 17, 1997, Pat. No. 5,770,207.

[51] Int. Cl.$^7$ .................................................. A61K 35/78
[52] U.S. Cl. ........................................................ 424/195.1
[58] Field of Search ........................................... 424/195.1

[56] References Cited

U.S. PATENT DOCUMENTS

| | | | |
|---|---|---|---|
| 5,273,754 | 12/1993 | Mann | 424/440 |
| 5,296,224 | 3/1994 | Schwabe | 424/195.1 |
| 5,569,458 | 10/1996 | Greenbeg | 424/195.1 |
| 5,569,459 | 10/1996 | Shlyankevich | 424/195.1 |
| 5,681,578 | 10/1997 | Sahley | 424/439 |

OTHER PUBLICATIONS

Munte et al, "Effects of Oxazepam and an Extract of Kava Roots (Piper Methysticum) on Event–Related potentials in a Word Recognition Task", *Neuropsychobiology* 1993:27, pp. 46–53.

Russell et al, "The Effects of Kava on Alerting and Speed of Access of Information from Long–Term Memory", *Bulletin of the Psychonomic Society*, 25(4), pp. 236–237 (1987).

M. Schmidt, "A Medicinal Plant from the South Seas", *PTA Heute*, vol. 8, No. 5, May 1994.

Mowrey, "The Scientific Validation of Herbal Medicine", *Keats Publishing*, Inc., New Canaan, CT, pp. 110, 163–166, 203–211, and 213–221 (1986).

Hoffmann, "The Herbal Handbook, A User's Guide to Medicinal Herbalism" Healing Arts Press, Rochester, VT, pp. 72–73 (1988).

The Merck Index, Tenth Ed., Merck & Co., Inc., Rahway, NJ, p. 812, entry #5512, and p. 1299, entry #8915 (1983).

Reid, "A Handbook of Chinese Healing Herbs", Shambhala Publications, Inc., Boston, MA, pp. 173–174, and 246–247 (1995).

Niu, X. et al., Yaoxue Xuebao, vol. 18(6), p. 416–421, abstract only, 1983.

Capasso, A. et al., Acta Therapeutic, vol. 21(2), p. 127–140, 1995.

Volz, H.P. et al., Pharmacopsychiat., vol. 30, p. 1–5, 1997.

Jussofie, A. et al., Psychopharamcology, vol. 116(4), p. 469–474, 1994.

Speroni, E. et al., Phytotherapy Research, vol. 10(Supplement 1), p. S92–S94, S98–S100, 1996.

Soulimani, R. et al., J. of Ethnopharmacology, vol. 57(1), p. 11–20, 1997.

Amdidouche–Hussain, D. et al., Drug Development and Industrial Pharmacy, vol. 23(12), p. 1223–1226, 1997.

*Primary Examiner*—Jean C. Witz
*Attorney, Agent, or Firm*—Benman & Collins

[57] ABSTRACT

A method is provided for reducing daily stress and anxiety in adults employing a novel dietary supplement composition that serves as a general relaxant. The supplement comprises pharmaceutical grade Kava root extract and at least one additional relaxing herb selected from the group consisting of Passion Flower, Chamomile Flower, Hops, and Schizandra Fruit. The most preferred composition of the dietary supplement, in capsule form, comprises: (a) about 200 mg pharmaceutical grade Kava root extract; (b) about 50 mg Passion Flower; (c) about 50 mg Chamomile Flowers; (d) about 50 mg Hops; (e) about 50 mg Schizandra Fruit; (f) about 5 mg talc; and (g) about 5 mg magnesium stearate. The method comprises administering the dietary supplement. A method is also provided for preparing the dietary supplement.

8 Claims, No Drawings

METHOD FOR REDUCING DAILY STRESS AND ANXIETY IN ADULTS

CROSS-REFERENCE TO RELATED APPLICATION

The present application is a continuation-in-part of application Ser. No. 08/818,931, filed Mar. 17, 1997 now U.S. Pat No. 5,770,207, issued Jun. 23, 1998.

BACKGROUND OF THE INVENTION

1. Field of the Invention

The present invention relates generally to dietary supplements, and, more particularly, to methods of preparing and administering a blend of Kava root extract and other relaxing herbs to reduce daily stress and anxiety in adults.

2. Description of Related Art

Throughout history, humans have ingested and otherwise consumed a wide variety of substances to effect relaxation, stress reduction, and an overall sense of well-being and tranquility. Examples of such substances include alcohol, marijuana, and prescription drugs such as valium. However, many such substances have significant undesirable side effects, including impairment of mental faculties, involuntary sleep, and the likelihood of user addiction. Thus, many relaxants are unsafe, especially for long-term usage.

One relaxant that does not typically exhibit any significant side effects is an extract from the Kava-kava root (hereinafter "Kava root"), which consists of the dried rootstock and/or shoots of *Piper methysticum Forst* (Family: Piperaceae). The Kava root extract is known to induce general relaxation in humans when orally ingested. An aqueous macerate of the Kava root known as "kava" or "kawa" has been used on islands in the South Pacific in social gatherings and religious rituals for three thousand years.

In recent years, the Kava plant has been scientifically scrutinized, with many of its active constituents being identified. The psychoactive ingredients of the Kava root have been identified as kavalactones, also known as kavapyrones. A total of fifteen kavalactones have been identified to date, including kavain, dihydrokavain (a.k.a. marindinin), methysticin, dihydromethysticin, yangonin, and desmethoxyyangonin. These compounds are neutral, nitrogen-poor compounds that may be specifically referred to as substituted d-lactones and substituted α-pyrones. The lactone ring is substituted by a methoxy group in the C-4 position, and the difference in the compounds lie in the substitution by a styryl residue (e.g., yangonin, desmethy-oxyyangonin, kavain, and methysticin) or by a phenyl residue (e.g., dihydrokavain and dihydromethysticin).

The particular kavalactones in a Kava root extract vary depending upon its origin. Further, the particular kavalactones present depend upon whether, in addition to rhizome parts, roots and stems of the plant are included in the extract. High quality extracts of the Kava root are sold based upon the total kavalactone content, rather than upon analysis of the individual lactones contained therein. The concentration ranges of total kavalactone levels in the Kava root extracts employed, e.g., in Germany are generally within the range of 30 to 55 wt %.

The Kava root extract lactones provide an anxiolytic effect, relieving nervous anxiety, tension, and restlessness, with their efficacy as a relaxant having been tested in clinical trials. The kavalactones also effect muscle relaxation. Studies have also shown that average single doses of Kava do not impair neurophysiological activity, as evidenced by such measuring indicia as recognition rates, event-related brain potentials, and driving ability (see, e.g., Münte et al, "Effects of Oxazepam and an Extract of Kava Roots (*Piper methysticum*) on Event-Related Potentials in a Word Recognition Task", *Neuropsychobiology* 1993:27, pp. 46–53 and Russell et al, "The Effect of Kava on Alerting and Speed of Access of Information from Long-term Memory", *Bulletin of the Psychonomic Society*, 25(4), pp. 236–37 (1987)). Further, kavalactones are non-addictive and do not induce involuntary sleep or effects of drunkenness.

Traditionally, Kava root is prepared for human consumption by pulverizing the plant material, mixing with water, and drinking the resulting liquid. Modern Kava root extracts are manufactured using ethanol as a solvent, as the kavalactones are readily soluble in ethanol. The extracted materials are in the form of a yellowish brown paste or powder, which is then tested to assure proper levels of kavalactones.

Today, Kava root extract is widely available in Germany and other European countries as an herbal supplement in the form of tablets, capsules, and dragées made of pharmaceutical grade extract. Ingestion of kavalactones in the form of drops is not desirable, given their bitter soapy taste. Typically, Kava root extract is commercially available in Europe with single doses containing 200 to 250 mg of extract with 30 wt % kavalactones, or about 60 to 75 mg kavalactones, and normal daily usage would be one to three capsules. Examples of available commercial extracts include the following trade designations, with the standardized milligrams of kavalactones in a dose indicated parenthetically if known: Antares®-120 (120 mg), Ardeydystin® forte (50 mg), Kava von ci (40 mg), Kavasedon® (25 mg per mL), Kavasporal® forte (50 mg), Kavatino® (25 mg), Laitin®-100 (70 mg), Kavain, Somnuvis®, Hewepsychon® duo (at least 24 mg per mL), Valeriana comp Hevert®, and Cefakava® 150 (35 mg) (see M. Schmidt, "A Medicinal Plant from the South Seas", *PTA heute*, Vol. 8, No. May 5, 1994)).

Although ingestion of the Kava root extract does not typically exhibit the serious side effects of other common relaxants, it likewise should not be used in the case of pregnancy or lactation. A known possible side effect of prolonged ingestion of the Kava root extract is a temporary yellow discoloration of the skin and appendages, upon observance of which one should cease intake of the herb. Other rare side effects include allergic skin reactions, gastrointestinal complains such as nausea and diarrhea, accommodation disorders (disorders of the ability of the eye to adjust to see at various distances), dilations of the pupil, and disturbances of the oculometer equilibrium.

Given the long-established beneficial calming effect of the Kava root extract and its rare incidence of associated side effects, it would be desirable to provide the Kava root extract in a dietary supplement improved over that already commercially available. The dietary supplement should enhance the general relaxant qualities offered by the Kava root extract without introducing any harmful side effects. It should be inexpensively manufactured and comply with all applicable governmental regulations.

SUMMARY OF THE INVENTION

In accordance with the present invention, a method is provided for reducing daily stress and anxiety in adults, comprising administering a dietary supplement that comprises Kava root extract and at least one additional relaxing herb selected from the group consisting of Passion Flower, Chamomile Flowers, Hops, and Schizandra Fruit. The present supplement therefore enhances the general relaxation achieved from the consumption of Kava root extract alone.

A method is also provided for preparing the foregoing formulation.

DESCRIPTION OF THE PREFERRED EMBODIMENTS

The dietary supplement of the invention comprises Kava root extract and at least one additional relaxing herb selected from the group consisting of Passion Flower, Chamomile Flowers, Hops, and Schizandra Fruit. These additional relaxing herbs have been used as relaxants both traditionally and in modern herbal medical practice, such that the resulting dietary supplement essentially enhances the general relaxant qualities offered by the Kava root extract without introducing any harmful side effects. The dietary supplement composition is preferably put into capsules using known technology, such that the recommended daily dose for an adult would be one to three capsules.

The Kava root extract employed is a pharmaceutical grade extract that is commercially available, e.g., from Meggenburg, a German manufacturer. Pharmaceutical grade Kava root extract manufactured in Germany is standardized for kavalactone content of about 30 wt % and contains the full spectrum of lactones found in the Kava plant. The pharmaceutical grade extract must pass extensive safety and efficacy procedures. The extract employed in the practice of the invention preferably has a minimum kavalactone content of about 30 wt %.

addition to Kava extract, the present dietary supplement contains at least one additional complementary relaxant herb to provide a calming and relaxing effect, among other benefits such as stress reduction, in addition to that effected by the Kava extract. The additional relaxant herb is selected from Passion Flower, Chamomile Flowers, Hops, and Schizandra Fruit, all of which are commercially available.

Preferably, a single dose or capsule of the present dietary supplement contains the following five relaxant herbs within the following ranges: (a) about 150 to 250 mg Kava root extract; (b) about 25 to 100 mg Passion Flower; (c) about 25 to 100 mg Chamomile Flowers; (d) about 25 to 100 mg Hops; and (e) about 25 to 100 mg Schizandra Fruit.

Passion Flower is a dry powdered herb deriving from *Passiflora incarnata*. Passion Flower has been traditionally used for it mild sedative effects; further, it advantageously has a pleasant taste and is surprisingly gentle. The plant contains a group of indole alkaloids and several flavonoids which are believed responsible for its sedative and analgesic effects. Both dried leaves and stems have been used to induce sleep, although the concentration of Passion Flower in the present dietary supplement is not enough to cause drowsiness.

Chamomile is a plant from the genus *Matricaria chemomilia*. Chamomile Flowers, in the form of a powdered herb, have been traditionally used in a tea for their sedative effect. It is now known that Chamomile Flowers contain a unique volatile oil, among other components, that account for their sedative effect.

Hops (*Humulus lupulus*) is a twisting vine of the mulberry family. Hops have traditionally been used in the form of a powdered herb for their calming and sedative properties. It has been shown that lupulin, which is a naturally-occurring constituent of hops, affects the central nervous system, causing a soothing and relaxing calm beginning about twenty minutes after ingestion.

Schizandra Fruit, which is a powdered herb deriving from *Schizandra chinensis*, has been classified as an adaptogen because of its ability to balance and regulate many functions of the body. It is preferably included in this formula as a balancing agent to combat the widespread effects of stress.

In addition to the Kava root extract and the additional complementary relaxing herb, the present dietary supplement may include various additives such as other vitamins and minerals, as well as inert ingredients such as talc and magnesium stearate that are standard excipients in the manufacture of tablets and capsules. Preferably, talc and magnesium stearate are included in the present dietary supplement. Most preferably, the Astac Brand 400 USP talc powder and the vegetable grade of magnesium stearate are employed.

The most preferred composition of the present dietary supplement is as follows: (a) 200 mg Kava root extract (30 % kavalactones); (b) 50 mg Passion Flowers powder; (c) 50 mg Chamomile Flowers powder; (d) 50 mg Hops powder; (e) 50 mg Schizandra powder; (f) 5 mg talc powder; and (g) 5 mg magnesium stearate.

The composition of the present invention is prepared by blending the components together, employing any of the methods commonly known in the art for preparing herbal supplements.

To study the effectiveness and safety of Kava using robust experimental designs, a study was devised to establish the effectiveness of the composition disclosed herein in a non-clinical sample of adults with daily stress and anxiety, during a 4-week, randomized, double blind, placebo-controlled study. A secondary aim was to establish the safety and tolerability of the composition disclosed herein throughout the duration of the study.

I. METHOD

A. Subjects

The subjects were recruited through advertisements in local health shops, pharmacies, and supermarkets. Referrals from family physicians were also accepted. They were included in the study if they met the following inclusionary criteria: (a) score of 1 SD above the mean on the State-Trait Anxiety Inventory; (b) age between 18 and 60; (c) good physical health; and (d) informed consent to participate in the study. They were excluded if they had the following: (a) endogenous depression, mental conditions of organic origin, or psychoses; (b) syndromes of dementia; (c) diseases of the kidneys, liver, lungs, heart, cardiovascular system as well as neoplasia, irrespective of its localization; (d) were pregnant; and (e) were on prescribed medications that may interact with the kavalactones or interfere with the assessment of efficacy and safety of the composition disclosed herein. These medications included the neuroleptics, antidepressants, sedatives, anxiolytics, and beta-blockers. Subjects were eligible for participation in the study if they discontinued their medication for a washout period of at least five half-life periods of their particular medication.

A total of 78 adults were screened for enrollment into the study. Of these, 11 did not meet the inclusionary and exclusionary criteria for enrollment and were excluded without further testing. The remaining 67 adults were enrolled in the study and randomized into Kavatrol™ (the most preferred composition of the present invention) and placebo groups within each gender (35 females [A1–A35] and 32 males [B1–B32]). Of the 67 subjects randomized into the trial, four subjects (A28, A30, B14, and B18) did not progress beyond baseline testing. One subject (B1) withdrew after a week on the trial and one withdrew (B15) after two weeks on the trial. Finally, one subject (A35) completed the trial but did not comply with the dosage regime. This subject was dropped from analysis because of medication non-compliance. Thus, the final sample consisted of 60 subjects (N=60).

Of the 60 subjects, 29 were in the Kavatrol™ group and 31 were in the placebo group. The subjects in the two groups had comparable age (t(58)=0.3; p>0.7; Kavatrol™ mean =37.0 years vs. placebo mean =36.0 years). The two groups had comparable numbers of males and females (Fisher's exact p=0.450g; Kavatrol™ male/female =12/17; placebo male/female =16/15). In the Kavatrol™ group, 21 of the 29 subjects were Anglo-American and in the placebo group 28 of 31 subjects were Anglo-American (p>0.2 by chi-square). The subjects in the two groups had comparable income (t(58)=0.53, p>0.6; Kavatrol™ mean =$25.9K vs. placebo means =$28.2K).

B. Study Design

This was a randomized, double blind, placebo-controlled, fixed-dose study of Kavatrol™, within a parallel groups design. Sixty-seven subjects who met the inclusionary and exclusionary criteria for entry into the study protocol were randomized into two parallel groups, experimental (Kavatrol™) and control (Placebo).

C. Dosage

Each subject received 2 capsules of Kava, 2 times a day (Kavatrol™ group), or 2 capsules of placebo, 2 times a day (control group). Kavatrol™, a non-prescription, commercially-available brand of Kava, was used as the active substance. Kavatrol™ is produced from dried Kava roots in a multistage extraction process. The extract is packaged in 200 mg capsules, with 30 % kavalactones (60 mg) in each capsule. Thus, each dose of Kavatrol• contained 120 mg kavalactones in 2×200 mg capsules. In clinical studies, no addiction, dependence, or other untoward effects have been reported at this and higher dosages of kavalactones. The placebos were identical to the Kavatrol™ capsules in all respects except that they were inert.

II. PROCEDURE

A. Baseline Measures

The following data were collected prior to the study: (a) degree of psychopathology as measured on the SCL-90; (b) medical history, including previous treatments for daily stress and non-clinical levels of anxiety; (c) sociodemographic information (i.e., race, gender, income, education); (d) self rating on the State-Trait Anxiety Inventory (STAI); (e) self rating on the Daily Stress Inventory (DSI); (f) self rating on the Untoward Effects Checklist; and (g) vital signs (i.e., blood pressure, heart rate, and respiratory rate). With the exception of efficacy and safety measures, the subjects completed the baseline measures only once.

B. Study Outcome Measures

The efficacy measures included the Daily Stress Inventory (DSI) and the State-Trait Anxiety Inventory (STAI). Subjects completed the STAI and DSI once each week, on the same day, for 4 weeks. The safety and tolerance of Kavatrol™ was measured using the Untoward Effects Checklist. The subjects completed this checklist once each week, on the same day of the week, for 4 weeks.

III. RESULTS

In terms of analysis, this was a repeated measures, double-blind study. The subjects were assigned either to Kavatrol™ or to placebo, and the effects of Kavatrol™ and placebo were assessed over a 4 week period. There were five time points for most assessment measures: baseline (week 0), and weeks 1, 2, 3, and 4. The dependent measures included daily stress on the DSI and anxiety on the STAI. The five content clusters on the DSI included: Interpersonal Problems (IP Sum), Personal Competency (PC Sum), Cognitive Stressors (CS Sum), Environmental Hassles (EH Sum), and Varied Stressors (VS Sum). The two major factors on the STAI included state (STAI-S) and trait (STAI-T) anxiety. Repeated measures analysis for each dependent variable is summarized. The independent variables were: group (the random assignment to Kavatrol™ or Placebo), gender (male or female), group×gender interaction, subjects nested within group×gender, week (the 5 time points for assessment), group×week interaction.

A. Effects on Daily Stress

1. Interpersonal Problems

IP sum values for the two groups were comparable at baseline (p>0.5). IP sum decreased across time for the subjects in the Kavatrol™ group but not for those in the placebo group (F[4, 228]=6.4, p<0.0001). The groups were significantly different at week 1 (p<0.0251), week 2 (p<0.0042), week 3 (p<0.0001), and at week 4 (p<0.0001). This showed that daily stress due to interpersonal problems decreased only for those subjects who were in the Kavatrol™ group.

2. Personal Competency

PC sum values for the two groups were not comparable at baseline (p<0.0067). That is, the subjects in the Kavatrol™ group had a higher LS mean (16.2) than those in the placebo group (13.1) at baseline. PC sum decreased across time for the subjects in the Kavatrol™ group but not for those in the placebo group (F[4, 228]=10.5, p<0.0001). The groups were not significantly different at week 1 (p >0.33) but were significantly different at week 2 (p<0.0027), week 3 (p<0.005), and at week 4 (p<0.0001). This showed that daily stress due to personal competency decreased only for those subjects who were in the Kavatrol™ group.

3. Cognitive Stressors

CS sum values for the two groups were comparable at baseline (p >0.66). CS sum decreased across time for the subjects in the Kavatrol™ group but not for those in the placebo group (F(4, 228)=6.5, p<0.0001). The groups were significantly different at week 1 (p<0.0024), week 2 (p<0.0001), week 3 (p<0.0001), and at week 4 (p<0.0001). This showed that daily stress due to cognitive stressors decreased only for those subjects who were in the Kavatrol™ group.

4. Environmental Hassles

EH sum values for the two groups were comparable at baseline (p>0.88). EH sum decreased across time for the subjects in the Kavatrol™ group but not for those in the placebo group (F[4, 226]=9.8, p<0.0001). The two groups were significantly different at week 1 (p<0.008), week 2 (p<0.0001), week 3 (p<0.0001), and at week 4 (p<0.0001). This those subjects who were in the Kavatrol™ group.

5. Varied Stressors

VS sum values for the two groups were not comparable at baseline (p<0.0001). The subjects in the Kavatrol™ group has a higher LS mean (24.3) than those in the placebo group (18.5). VS sum decreased across time for the subjects in the Kavatrol™ group but not for those in the placebo group (F[4, 226]=19.5, p<0.0001). The two groups were not significantly different at week 1 (p>0.23) but were significantly different at week 2 ($p<0.0001$), week 3 ($p<0.0001$), and at week 4 ($p<0.0001$). This showed that daily stress due to varied stressors decreased only for those subjects who were in the Kavatrol™ group.

6. Weekly Stress Index

WSI sum values for the two groups were not comparable at baseline ($p<0.0098$). The subjects in the Kavatrol™ group had a higher LS mean (92.8) than those in the placebo group (83.5). WSI sum decreased across time for the subjects in the Kavatrol™ group but not for those in the placebo group ($F[4, 226]=33.2$, $p<0.0001$). The two groups were significantly different at week 1 ($p<0.0001$), week 2 ($p<0.0001$), week 3 ($p<0.0001$), and at week 4 ($p<0.0001$). This showed that daily stress summed for each week decreased only for those subjects who were in the Kavatrol™ group.

B. Effects on Anxiety

1. State Anxiety

STAI-S values for the two groups were comparable at baseline ($p>0.69$). STAI-S decreased across time for the subjects in the Kavatrol™ group but not for those in the placebo group ($F[4, 227]=44.6$, $p<0.0001$). The two groups were significantly different at week 1 ($p>0.0001$), week 2 ($p<0.0001$), week 3 ($p<0.0001$), and at week 4 ($p<0.0001$). The state anxiety is amenable to change due to environmental, psychological, and personal circumstances of the individual. The data showed that state anxiety decreased on a weekly basis only for those subjects who were in the Kavatrol™ group.

2. Trait Anxiety

STAI-T values for the two groups were not comparable at baseline ($p>0.0058$). STAI-I was measured only at baseline and at the end of study. Trait anxiety decreased across time ($F[1, 57]=8.8$, $p<0.0045$) in equal amounts for the subjects in each of the two groups ($p>0.0585$). There was no significant difference in trait anxiety for the subjects in the two groups at the end of the study ($p>0.2893$). The trait anxiety is thought to be a fairly fixed attribute and thus not amenable to dramatic change. There was no difference in trait anxiety for the subjects in the two groups by the end of the study.

C. Untoward (Side) Effects

Untoward sum values for the two groups were comparable at baseline ($p>0.54$). Untoward sum decreased across time for subjects both in the Kavatrol™ and the placebo groups ($F[4, 228]=8.6$, $p<0.0001$). There was no significant group×week interaction ($F[4, 228]=1.48$, $p<0.2100$) so it is not appropriate to test for group differences at each time point. These data suggest that when compared to baseline levels, none of the subjects experienced an increase in the 27 side effects that were measured as a consequence of taking Kavatrol™ or placebo capsules.

IV. DISCUSSION

This study showed that Kavatrol™ reduced daily stress and non-clinical levels of anxiety in adults when compared to baseline and placebo conditions. To the best of the inventor's knowledge, this is the first study to show that Kava reduces the stress that is associated with the daily hassles of life. In this study, the commercially-available Kavatrol™ brand of Kava was used and it was found that overall stress decreased as a function of the time that a person was on the herbal product. That is, greater reductions were evident with longer usage of Kavatrol™. Kavatrol™ was effective in producing statistically significant reductions in stress in each of the five daily stressor clusters: interpersonal problems, personal competency, cognitive stressors, environmental hassles, and other varied stressors of urban life.

In the present study, Kavatrol™ was used in a dosage of 240 mg/day of kavalactones. The results showed that state anxiety of the subjects on Kavatrol™ decreased from baseline to week four, and the reduction was statistically significant when compared to the reduction in anxiety reported by the subjects in the placebo group. As expected, the level of trait anxiety for the Kavatrol™ and the placebo groups did not differ significantly at the end of the trial. These data show that state anxiety can be significantly reduced on a moderate dose of Kavatrol™ without any side effects. Kava does not have the untoward effects associated with other anxiety reducers, such as benzodiazepines; it is not addictive and does not lead to dose tolerance.

Thus, there has been disclosed a method of reducing daily stress and anxiety in adults, employing a dietary supplement comprising Kava root extract and at least one additional relaxing herb selected from the group consisting of Passion Flowers, Chamomile Flowers, Hops, and Schizandra. It will be readily apparent to those skilled in the art that various changes and modifications of an obvious nature may be made without departing from the spirit of the invention, and all such changes and modifications are considered to fall within the scope of the invention as defined by the appended claims.

What is claimed is:

1. A method of reducing daily stress and anxiety in adults comprising administering, in capsule form, a dietary supplement comprising the following components:
   a. about 150 to 250 mg pharmaceutical grade Kava root extract;
   b. about 25 to 100 mg Passion Flower;
   c. about 25 to 100 mg Chamomile Flowers;
   d. about 25 to 100 mg Hops; and
   e. about 25 to 100 mg Schizandra Fruit.

2. The method of claim 1 wherein said components are provided in a total of four capsules, administered as two capsules twice per day.

3. The method of claim 1 wherein said dietary supplement further comprises at least one additive selected from the group consisting of talc and magnesium stearate.

4. The method of claim 2 wherein said dietary supplement further comprises about 5 mg talc and about 5 mg magnesium stearate.

5. The method of claim 4 wherein said components are provided in a total of four capsules, administered as two capsules twice per day.

6. A method of reducing daily stress and anxiety in adults comprising administering, in capsule form, a dietary supplement comprising the following components:
   a. about 200 mg pharmaceutical grade Kava root extract;
   b. about 50 mg Passion Flower;
   c. about 50 mg Chamomile Flowers;
   d. about 50 mg Hops; and
   e. about 50 mg Schizandra Fruit.

7. A method of preparing a dietary supplement for reducing daily stress and anxiety in adults, comprising blending together pharmaceutical grade Kava root extract, Passion Flower, Chamomile Flowers, Hops, and Schizandra Fruit, in capsule form, comprising the following components:
   a. about 150 to 250 mg Kava root extract;
   b. about 25 to 100 mg Passion Flower;
   c. about 25 to 100 mg Chamomile Flowers;
   d. about 25 to 100 mg Hops; and
   e. about 25 to 100 mg Schizandra Fruit.

8. The method of claim 7, wherein said dietary supplement further comprises at least one additive selected from the group consisting of talc and magnesium stearate.

* * * * *